US006248343B1

(12) United States Patent
Jampani et al.

(10) Patent No.: US 6,248,343 B1
(45) Date of Patent: Jun. 19, 2001

(54) THERAPEUTIC ANTIMICROBIAL COMPOSITIONS

(75) Inventors: Hanuman B. Jampani, Grapevine; Jerry L. Newman; Timothy Ellis, both of Arlington, all of TX (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/460,031

(22) Filed: Dec. 13, 1999

Related U.S. Application Data

(63) Continuation-in-part of application No. 09/009,596, filed on Jan. 20, 1998, now Pat. No. 6,022,551.

(51) Int. Cl.$^7$ .......................... A01N 25/00; A61K 35/78; A61K 7/00; A61K 31/155; A61K 31/14

(52) U.S. Cl. ................ 424/405; 424/195.1; 424/401; 514/635; 514/642; 514/724; 514/828; 514/859; 514/944

(58) Field of Search ..................... 424/401, 405, 424/195.1; 514/635, 642, 724, 828, 859, 944

(56) References Cited

U.S. PATENT DOCUMENTS

| | | |
|---|---|---|
| 2,798,053 | 7/1957 | Brown . |
| 3,133,865 | 5/1964 | Richardson et al. . |
| 3,886,277 | 5/1975 | Randebrockt et al. . |
| 3,932,655 | 1/1976 | Conn . |
| 3,954,794 | 5/1976 | Herzog et al.. . |
| 4,006,218 | 2/1977 | Sipos . |
| 4,134,412 | 1/1979 | Gross et al. . |
| 4,197,318 | 4/1980 | Sipos . |
| 4,202,881 | 5/1980 | Gross et al. . |
| 4,257,907 | 3/1981 | Langguth et al. . |
| 4,268,424 | 5/1981 | Hall et al. . |
| 4,303,543 | 12/1981 | Mansy . |
| 4,321,257 | 3/1982 | Sipos . |
| 4,326,997 | 4/1982 | Willis et al. . |
| 4,340,756 | 7/1982 | Dybas et al. . |
| 4,423,041 | 12/1983 | Clum et al. . |
| 4,426,310 | 1/1984 | Verunica . |
| 4,464,293 | 8/1984 | Dobrin . |
| 4,474,807 | 10/1984 | Gerhardt et al. . |
| 4,668,513 | 5/1987 | Reichert . |
| 4,690,821 | 9/1987 | Smith et al. . |
| 4,804,750 | 2/1989 | Nishimura et al. . |
| 4,816,451 | 3/1989 | Schriewer et al. . |
| 4,849,455 | 7/1989 | Eggers et al. . |
| 4,923,862 | 5/1990 | Hirota . |
| 4,956,170 | 9/1990 | Lee . |
| 4,957,908 | 9/1990 | Nelson . |
| 4,966,754 | 10/1990 | Purohit et al. . |
| 5,004,598 | 4/1991 | Lochhead et al. . |
| 5,019,604 | 5/1991 | Lemole . |
| 5,053,407 | 10/1991 | Hayakawa et al. . |
| 5,098,717 | 3/1992 | Blackman . |
| 5,100,672 | 3/1992 | Gueret et al. . |
| 5,109,019 | 4/1992 | Lehmann et al. . |
| 5,164,107 | 11/1992 | Khan et al. . |
| 5,180,061 | 1/1993 | Khan et al. . |
| 5,180,749 | 1/1993 | Cusack et al. . |
| 5,188,756 | 2/1993 | Baker et al. . |
| 5,236,699 | 8/1993 | Libin . |
| 5,244,666 | 9/1993 | Murley . |
| 5,288,486 | 2/1994 | White . |
| 5,292,529 | * 3/1994 | Gregory et al. ................... 424/59 |
| 5,298,242 | 3/1994 | Vanlerberghe et al. . |
| 5,308,890 | 5/1994 | Snyder . |
| 5,326,492 | 7/1994 | Hodam, Jr. . |
| 5,335,373 | 8/1994 | Dangman et al. . |
| 5,336,305 | 8/1994 | Staats . |
| 5,401,741 | 3/1995 | Sato et al. . |
| 5,403,587 | 4/1995 | McCue et al. . |
| 5,403,864 | 4/1995 | Bruch et al. . |
| 5,416,109 | 5/1995 | Donofrio et al. . |
| 5,420,104 | * 5/1995 | Holzner et al. ..................... 512/2 |
| 5,439,681 | 8/1995 | Khan et al. . |
| 5,492,932 | 2/1996 | Kundsin . |
| 5,512,199 | 4/1996 | Khan et al. . |
| 5,540,853 | 7/1996 | Trinh et al. . |
| 5,567,428 | 10/1996 | Hughes . |
| 5,591,442 | 1/1997 | Diehl et al. . |
| 5,607,681 | 3/1997 | Galley et al. . |
| 5,622,694 | 4/1997 | Torgerson et al. . |
| 5,626,837 | 5/1997 | Shimada et al. . |
| 5,629,006 | 5/1997 | Hoang et al. . |
| 5,661,170 | 8/1997 | Chodosh . |
| 5,665,742 | 9/1997 | Mori et al. . |
| 5,681,802 | 10/1997 | Fujiwara et al. . |
| 5,683,683 | 11/1997 | Scafidi . |
| 5,709,872 | 1/1998 | Van Rees . |
| 5,725,845 | 3/1998 | Krog et al. . |
| 5,750,579 | 5/1998 | Kamishita et al. . |
| 5,759,969 | 6/1998 | Tsaur et al. . |
| 5,767,163 | 6/1998 | Kundsin . |
| 5,871,763 | * 2/1999 | Luu et al. ........................ 424/402 |
| 5,888,520 | * 3/1999 | Toma et al. ...................... 424/401 |
| 6,015,574 | * 1/2000 | Cannell et al. ................... 424/450 |
| 6,022,551 | * 2/2000 | Jampani et al. ................... 424/405 |

FOREIGN PATENT DOCUMENTS

| | | |
|---|---|---|
| 600269 | 5/1987 | (AU) . |
| 0 099 209 | 1/1984 | (EP) . |
| 0 231 080 | 4/1987 | (EP) . |

(List continued on next page.)

OTHER PUBLICATIONS

Chemical Abstracts, Jones, M.N. et al., "The Use of Phospholipid Liposomes for Targeting to Oral and Skin–Associated Bacteria", vol. 122, No. 8, pp. 381–389, Feb. 1995.
Journal of Clinical Microbiology, Lee W. Bush, Leslee M. Benson, and John H. White, "Pig Sin as Test Substrate for Evaluating Topical Antimicrobial Activity", Sep. 1986. p. 343–348.

Primary Examiner—Shelley A. Dodson
Assistant Examiner—Marina Lamm
(74) Attorney, Agent, or Firm—Theodore Shatynski

(57) ABSTRACT

Antimicrobial alcohol-containing compositions and methods of using the compositions to disinfect surfaces and provide therapeutic benefits are disclosed.

22 Claims, No Drawings

FOREIGN PATENT DOCUMENTS

| | | |
|---|---|---|
| 0 223 681 B1 | 5/1987 | (EP) . |
| 0 252 278 B1 | 1/1988 | (EP) . |
| 0 440 966 B1 | 8/1991 | (EP) . |
| 0 604 848 B1 | 7/1994 | (EP) . |
| 0 640 285 B1 | 6/1995 | (EP) . |
| 0 692 192 A1 | 1/1996 | (EP) . |
| 0 505 935 B1 | 2/1998 | (EP) . |
| 2 236 167 | 12/1998 | (GB) . |
| WO90/11342 | 10/1990 | (WO) . |
| WO94/27436 | 12/1994 | (WO) . |
| WO95/05737 | 3/1995 | (WO) . |
| WO97/35475 | 10/1997 | (WO) . |
| WO98/02139 | 1/1998 | (WO) . |
| WO98/17773 | 4/1998 | (WO) . |
| WO98/20094 | 5/1998 | (WO) . |
| WO98/20095 | 5/1998 | (WO) . |

* cited by examiner

THERAPEUTIC ANTIMICROBIAL COMPOSITIONS

This patent application is a continuation in-part of U.S. patent application, Ser. No. 09/009,596, now U.S. Pat. No. 6,022,551, entitled ANTIMICROBIAL COMPOSITION, filed Jan. 20, 1998, now U.S. Pat. No. 6,022,551 which is assigned to the assignee of the present invention and incorporated by reference.

This application is related to U.S. patent applications, Ser. No. 09/460,014, entitled DEEP PENETRATING ANTIMICROBIAL COMPOSITIONS; 09/460,013, entitled NOVEL SKIN DISINFECTION PROCEDURES and 09/460,012, entitled STABILIZED ANTIMICROBIAL SYSTEMS AND METHODS OF MAKING THE SAME, all concurrently filed herewith and which are assigned to assignee of the present invention and incorporated by reference as if fully set forth herein.

The present invention relates antimicrobial compositions which additionally provide therapeutic benefits to the skin.

BACKGROUND OF THE INVENTION

In addition to application of antimicrobial composition to hands, skin site preparation (surgical, catheter, wound, and patient) is a key component of integrated infection control program in all hospitals. Similarly in non-surgical situations, acne (acne vulgaris affecting the hair follicles and oil-secreting glands of the skin and manifesting as blackheads (comedones), whiteheads (pustules), and inflammation (papules), and acne conglobata- a more severe form, with deep cyst formation and subsequent scarring) is the most common of all skin problems and widely seen in younger population. Also, skin lesions (e.g., pseudofolliculitis barbae ("PFB")) before, during or after shaving are a major problem.

Current skin prep products used in hospitals are prone to some disadvantages such as: 1) irritation; 2) potential for cellular oxidative reactions (Iodine and its derivatives); 3) poor antimicrobial activity against resistant microbes and emerging organisms; 4) lack of aesthetics; 5) Lack of residual activity (iodine based formulations); and 6) lack of colorants for site identification (chlorhexidine gluconate "CHG" formulations). Similarly salicylic acid or benzoyl peroxide-based formulations cause either irritations or oxidative reactions. These reactions could potentially generate materials such as super oxides and other mutagens, and as a result there is a need to develop compositions that are much safer to skin with potential staining and anti-inflammatory properties while exhibiting antimicrobial activity against inflammation, odor or disease causing pathogens.

The significance of proper prepping and usage of antimicrobials is on the rise, as nosocomial infections are becoming a major problem to health care organizations. Iodine and iodine-based products are being used due to their immediate activity against resident flora and also inherent staining properties as a site indicator for prepping or for needle insertion. Advancement in iodine based technology has occurred, and as a result number of new technologies emerged to overcome certain negative features of iodine. However, iodine or iodine-based technologies do not offer any residual activity, as a result the regrowth of resident flora is noted above the baseline over period of time. This feature limits the usage of iodine based products where persistent antimicrobial activity is an essential feature on moist and dry areas. It is well established that iodine based products exhibit activity by oxidizing microbial cellular components, while showing undesired irritations and sensitization's on human skin. At present combination of iodine and alcohol preparations are being developed to compete with CHG market. It is noteworthy that alcohol and iodine combination may increase irritation potential unless the blend is formulated in an emollient or gel based matrix, and yet, the combination may not exhibit residual activity comparable to CHG formulations. Though CHG based formulations are currently marketed as skin preps, the limiting factor again would be potential irritations as these products are being used as leave on or wipe-off and rinse-off products.

The negative aspects of current products clearly demands for more potent yet gentle formulations or combinations that display antimicrobial efficacy, staining properties, anti-inflammatory features to reduce any inflammation around surgical site, needle site or non-surgical sites.

Examples of non-surgical sites/inflammations include acne, pseudofolliculitis, infected areas by fungus, insects, viruses, sun burns, rash, dermatitis, *Tinea pedis* (Athlete's foot), scleroderma, psoriasis, atopic dermatitis, genital infections, dermatoses and itching, skin cancer, bacterial infections, alopecia and other infections.

Plants and plant products have been used historically as chemopreventative products. In recent years, advancement in technology, miniaturization and high throughput screening has dramatically changed the bioactive compound discovery process. Number of active molecules were identified and with modifications in structures/functionalities several compounds have been commercialized to improve human health. The best recent examples are taxol from *Taxus brevifolia*, vincristine and vinblastin from Vinca rosea, and several other compounds. In recent years, naturals/botanicals/herbal products gained momentum in cosmetic and dietary product development. Natural products have several advantages over synthetic compounds in their slow and steady action with excellent safety profile. The research and development of novel compounds from natural source (Cosmeceuticals and Neutraceuticals) and evaluation of such compounds for their biological activity has seen all over the world. Most of the plant mixtures are ingested as dietary supplements but some are applied topically to treat various skin conditions. Ayurveda, the ancient Indian Materia Medica believes that such combinations produce a synergism where by the beneficial effects of the whole is greater than the sum of its parts. Among several plants or plant extracts, the following are known to exhibit favorable effects on skin conditions such as anti-irritant, wound healing and skin lesions:

anti-irritant: Amalaki (Indian gooseberry)
wound healing and skin lesions: Gotukola
cancerous lesions-breast, skin, vulva: Curcum longa
antiseptic/astringent: Guggui (a gum resin),
Hydrastis canadensis (Golden seal)
anti-inflammatory: Licorice
skin ulcer, boils: Shallaki
drug delivery system: Mango butter
speeding cellular renewal: high mineral content of many muds There is overwhelming interest in natural ingredients for cleansing, coloration, and treatment of skin, wounds, scalp and hair. Since ancient times, humans have used preparations derived from plants to dye their hair, and skin and to heal their wounds.

The tropical plant, *Curcuma longa* is widely consumed in Asia for variety or purposes. Turmeric (*Curcuma longa*) has been used to combat a variety of ailments such as cancer prevention. Volatile oil from the rhizomes displayed mosquitocidal activity. It is reported in the literature that ethyl acetate (EtOAC) extract yielded Curcumin 1, 2, and 3 which have shown inhibitory activity against topoisomerase -I and -II. Curcumin or turmeric yellow has a MW 368 and is the dyestuff from the root of curcuma longa and it is insoluble in water but soluble in alcohol. The striking feature of the extract is intense coloring characteristic with anti-inflammatory, anti-cancer, and wound healing properties. Similarly, extracts and pure compounds of *Hydrastis canadensis* (Golden seal), *Croccus sativus* (Saffron) and *Alkanna tinctoria* (Henna root) also known as cosmetic dyes due to their astringent properties. Though these features are known in the literature the coloring features of these extracts or pure compounds have not been used to develop preparations to prep surgical, catheter, wound and other non-surgical sites. In particular, these features have not been explored in combination with alcohol based gels such as gels containing naturally derived biomimmetic phospholipids along with preservatives to offer the following benefits:

immediate and Persistent antimicrobial activity against skin flora (resident and transient )

staining properties to locate the surgical site or catheter site.

anti-inflammatory properties (anti-acne, pseudofolliculitis/skin lesions)

reduction in skin prep time wound cleansers

Accordingly, there is a continuing desire for antimicrobial compositions that are antimicrobially effective while also having therapeutic (anti-inflammatory) benefits and, when desired, staining properties to indicate a disinfected site.

SUMMARY OF THE INVENTION

One embodiment of the present invention provides an antimicrobial composition comprising:

a) an antimicrobial selected from the group consisting of more than 30% by volume alcohol, an effective amount of triclosan and mixtures thereof;

b) an effective amount of phenoxy ethanol, an effective amount of benzalkonium chloride or benzethonium chloride; and an effective amount of PHOSPOLIPID CDM; and c) an effective amount of a naturally occurring plant or extract thereof.

In a second embodiment of the invention, the antimicrobials are further provided with an effective amount of triclosan, GERMALL PLUS and GERMABEN II. Additionally, the antimicrobial composition optionally also contains an effective amount of PHOSPOLIPID PTC.

In yet another embodiment of the present invention, the antimicrobial compositions also demonstrated surprising therapeutic activity in treating bacterial inflammations of the skin such as acne, pseudofolliculitis (PFB) and skin lesions.

Advantages of this invention include therapeutic benefits in addition to antimicrobial properties: enhanced anti-inflammatory properties with natural ingredients; reduced irritation potential with synergistic combination as compared to conventional skin preparations; multifunctional properties with staining features; other advantages of this invention (with-or without enhancing natural plants or extracts thereof) include an antimicrobial hand gel as an anti-acne product; as a therapeutic shaving gel to treat or heal skin lesions and prevent bacterial contamination; as a gel for treatment of Pseudofolliculitis barbae; as a gel for antiviral applications; as a no-rinse antimicrobial skin or dermal cleanser, urinary and fecal incontinent cleanser, deodorizer, antimicrobial wound cleanser, (burn patients, infection control during skin grafting procedure, skin/hand disinfection during plastic surgeries, to remove exudates around wound areas) and antimicrobial moisturizing lotion and/or gel.

Another advantage of the present invention includes a method for controlling both intact and broken skin inflammations including local redness, local pain, local odor (i.e., foot and armpit odor), and increased exudate.

DETAILED DESCRIPTION OF THE INVENTION

The naturally occurring plants and plant extracts useful in this invention are any such compositions which impart therapeutic (healing) benefits and/or the coloring (staining) properties.

As used herein, the expression "a naturally occurring plant or extract thereof" is intended to encompass both crude and/or purified forms of plants and extracts thereof as one skilled in the art will appreciate that plants and their extracts exist both in crude and purified form. Furthermore, "a naturally occurring plant or extract thereof" is intended to include those pure or crude plants and plant extracts derived by using organic solvents. Thus, oils derived from the plant or extract are excluded from the scope of the expression "a naturally occurring plant or plant extract".

Examples of naturally occurring plants and plant extracts that possess both therapeutic and coloration benefits include: *Curcuma longa; Hydrastis canadensis* (Golden seal); and *Croccus sativa* (Saffron).

Examples of naturally occurring plants and plant extracts that are colorless but possess therapeutic benefits include: Tea tree (*Melaleuca alternifolia*), Evening primrose (*Oenothera biennis*), Red clover (*Trifolium pratense*) and Aloe (Aloe vera).

Examples of naturally occurring plants and plant extracts that possess coloring properties include *Alkanna tinctoria* (Henna root).

As apparent t o one skilled in the art, the effective amount of naturally occurring plants or plant extracts used in this invention may vary according to several factors such as the desired degree of therapeutic benefit and/or coloration. However, good results have been achieved by using from about 1.0 to about 25.0, preferably from about 2.0 to about 15, most preferably from about 2.0 to about 5.0 percent by weight of the composition of the plant or plant extract.

A surprising result concerning the alcohol-containing compositions even without the presence of naturally occurring plant or plants extracts is that such compositions provide therapeutic benefits, particularly anti-inflammatory benefits.

The alcohol content of the present invention is greater than about 30 percent by volume, typically from about 55 to about 90 percent by volume, preferably from 60 to about 85 and most preferably from 60 to about 70% by volume of the composition. The alcohols useful in the present invention include, ethyl alcohol, iso-propyl alcohol, n-propyl alcohol and combinations thereof. Ethyl alcohol may be used as the only alcohol in the invention or in another embodiment the alcohol content in the invention provides ethyl alcohol from about 40 to about 70% by volume, iso-propyl alcohol from about 5 to about 25% by volume and n-propyl alcohol from about 5 to about 25% by volume.

Triclosan may be employed from about 0.1 to about 2.0, preferably from about 0.2 to about 1.0 by weight.

The present invention contains a mixture of an effective amount of antimicrobials phenoxyethanol alcohol, PHOSPHOLIPID CDM, benzalkonium chloride, and preferably GERMALL PLUS and GERMABEN II. Phenoxy ethanol is used from about 0.25 to about 5.0 percent by weight, preferably from about 0.3 to about 2.0, most preferably at about 0.3 to about 1.0 percent by weight. PHOSPHOLIPID CDM is used from about 0.01 to about 1.0, preferably from about 0.03 to about 0.7, most preferably 0.5 percent by weight. *Benzethonium chloride* or preferably benzalkonium chloride is used from about 0.02 to about 1.0, preferably from about 0.08 to about 0.5, most preferably about 0.1 to about 0.2 percent by weight.

Other antimicrobial compositions have been found to particularly effective in improving the efficacy of the invention. These compositions include triclosan, PHOSPHOLIPID PTC, GERMALL PLUS and GERMABEN II.

The amount of GERMALL PLUS and GERMABEN II, independently provided in the invention varies from about 0.05 to about 0.5 with 0.1 percent by weight preferred. In the present invention the use of GERMALL PLUS and GERMABEN II together has been found to be highly effective. The ratio of the two materials when employed together is from about 0.1:1 to 1:0.1 and most preferably 1:1 weight ratio.

In addition to the antimicrobial compositions recited above, other antimicrobials may be employed with the present invention including nisin, bis-guanides, chlorhexidine gluconate, chlorhexidine digluconate, chlorhexidine diacetate, chlorhexidine dihydrochloride, triclosan, sodium hydroxy methyl glycinate, octanoyl collagenic acid, cetyl pyridinium chloride, phenol, iodine, parachlorometaxylenol (PCMX), polymeric quaternary ammonium compounds, their combinations and the like. The antimicrobial compositions are typically added at a level of from 0.1 to about 4.0 percent by weight.

Other preferred ingredients employed in the invention include PHOSPHOLIPID PTC, which is employed from about 0.01 to about 1.0, preferably from about 0.02 to about 0.08, and most preferably about 0.05 percent by weight. Australian tea tree oil and lemon grass oil are used in 1:1 ratio from about 0.5 to about 10.0, preferably from about 1.0 to about 7.0, and most preferably 5.0 weight percent.

One highly preferred embodiment of the invention provides more than 40% by weight alcohol, an effective amount of phenoxy ethanol, an effective amount of benzalkonium chloride, an effective amount of GERMALL PLUS, an effective amount of GERMABEN-II, and an effective amount of PHOSPHOLIPID CDM. Additionally, the antimicrobial composition optionally also contains an effective amount of PHOSPHOLIPID PTC.

In another preferred embodiment the antimicrobial mixture comprises greater than about 40% by weight alcohol, an effective amount of phenoxy ethanol, an effective amount of benzalkonium chloride, an effective amount of triclosan, an effective amount of GERMALL Plus, an effective amount of GERMABEN-II, and an effective amount of PHOSPHOLIPID CDM.

In yet another preferred embodiment of the invention the antimicrobial mixture contains greater than about 40% by weight alcohol, an effective amount of phenoxy ethanol, an effective amount of benzalkonium chloride, an effective amount of benzethonium chloride, an effective amount of triclosan, an effective amount of GERMALL Plus, an effective amount of GERMABEN-II, and an effective amount of PHOSPHOLIPID CDM.

In another highly preferred embodiment of the invention the antimicrobial mixture is greater than 40% by weight a mixture of alcohols such as ethyl alcohol, iso-propyl alcohol, and n-propyl alcohol, a mixture of two essential oils such as Australian tea tree oil, and lemon grass oil, an effective amount of phenoxy ethanol, an effective amount of benzalkonium chloride, an effective amount of triclosan, an effective amount of GERMALL plus, an effective amount of GERMABEN-II, and an effective amount of PHOSPHOLIPID CDM. Additionally, the antimicrobial composition optionally also contains an effective amount of Vitamin E linoleate.

The antimicrobial compositions of the present invention are found to possess immediate and persistent activity over time. The compositions of the present invention also compare favorably with antimicrobial compositions which contain high levels of chlorhexidine gluconate or commercial products such as HIBISTAT and HIBICLENS, available from ZENECA Pharmaceuticals, which are commonly being used for disinfecting surgical scrubs, hand disinfectants and in preoperative preparation of patients.

It is known in the art that chlorhexidine gluconate formulations exhibit a great build-up in activity between washes 1 and 7. This increase in activity is believed to be caused by its polar structure and its ability to attach to skin. After ten washes and neutralization with suitable inactivator, the activity of chlorhexidine gluconate falls significantly (approximately 30–50%) at wash 10, when testing is performed in accordance with a Health Care personnel hand wash protocol. Surprisingly, the compositions of the present invention provide more persistent antimicrobial activity than these other well-known antimicrobial agents.

Another advantage of the present invention is the residual activity provided by the antimicrobial product. The present invention provides effective protection against a broad spectrum of organisms, including gram positive, gram negative, yeast and fungi both at the initial application time, but also after an extended period of time. We have found that unlike other antimicrobial compositions which are initially effective in killing microbes but which quickly lose their efficacy in about one hour. Surprisingly, the present invention is effective in preventing the appearance of microbes for an extended periods of time, such as greater than two hours, preferably for about three or four hours or more.

It is preferable to include other ingredients in the formulation to enhance the efficacy of the antimicrobial composition. Included in this are essential oils to improve the rate at which the antimicrobial composition works as well as its residual activity. Suitable essential oils include Australian tea tree oil, lemongrass oil, thyme oil, lavender oil and clove oil and combinations thereof. Essential oils are used to increase the emolliency, moisturization, emollient and penetration properties of the present invention. Typically these oils are incorporated at the level of from about 1 to about 10 weight percent, and most preferably at about 5 weight percent based upon the total composition.

The present invention also employs thickening agents of acrylic acid which are crosslinked with an unsaturated polyfunctional agent such as polyallyl ether of sucrose. These acrylic acid functionalized polymers, commonly known as carbomers, are disclosed in U.S. Pat. Nos. 2,798,053 and 3,133,865 herein incorporated by reference.

The selection of the proper carbomer provides the antimicrobial formulation with the desired viscosity values. In order to have the desired feel the viscosity of the formulation must have a value of greater than about 5,000 centipoise. More preferably the formulations will have a viscosity of from about 9,000 to about 22,000 and most preferably from about 11,000 to about 20,000 centipoise as measured at 25° C.

A thickening agent, which is an addition agent comprised of an acrylic acid polymer crosslinked with an unsaturated polyallyl ether of sucrose is employed. The polymers are used in an amount sufficient to obtain a gelled composition of viscosity in the desired range.

A number of these polymers, known in the art as carbomers are commercially marketed by B.F. Goodrich, (Cleveland, Ohio) such as CARBOPOL® 934, 940 and 941; and by R.I.T.A. (Crystal Lake, Ill.)as ACRITAMER® 934, 940 and 941, respectively. Typically the carbomer compounds are used from about 0.2 to about 2.0 percent by weight, and are preferably employed at a level of from about 0.4 to about 0.7 by weight of the total antimicrobial composition.

A preferred carbomer polymer, among several preferred carbomers is R.I.T.A. ACRITAMER® 505E, a polyvinyl carboxy polymer crosslinked with ethers of pentaerythritol. ACRITAMER® 505E is preferred as a gelling agent or viscosity enhancer because it provides a transparent or translucent gel in the present invention.

The most preferred carbomer is ULTREZ® 10 (available from BF Goodrich) a modified copolymer having a major portion of a mono olefinically unsaturated carboxylic acid monomer or its anhydride of 3 to 6 carbon atoms and a minor portion of a long chain acrylate or methacrylate ester monomer. The polymer is predominately acrylic acid and a smaller amount of a long chain acrylate monomer. The polymer is described in U.S. Pat. No. 5,004,598, hereby incorporated by reference in its entirety.

Another particularly preferred group of ingredients in the present invention are tack modifiers such as silicone waxes, stearoxy trimethyl silane, cyclomethicone, cetyl lactate, and alkyl lactates, (typically lengths $C_{12}$–$C_{15}$). Moisturizers such as glycerin, water, lipids, waxes and the like are also helpful when employed in the present invention. Other solvents are also employed, such as propylene glycol, in order to provide for a more stable formulation.

Other ingredients which may be added to the compositions include fragrances, emollients, pH adjusters, viscosity modifiers such as acrylic polymers, gums, xanthan gums and the like; transdermal enhancers, surfactants, dyes, colors and the like. These ingredients are well known in the art and are disclosed for example in U.S. Pat. No. 5,403,864 and 5,403,587. The remainder of the present formulation is made up of water, preferably deionized water. Water typically makes up from 10 to about 40% by weight of the antimicrobial composition.

The following formulation possesses highly effective antimicrobial properties.

1. Ethyl alcohol (40–70%), Isopropyl alcohol (20–25%), n-Propyl alcohol (5–10%).
2. Diisobutyl Phenoxy Ethoxy Ethyl Dimethyl Benzyl Ammonium chloride (0.05–0.5%), commonly known as benzethonium chloride.
3. triclosan, commonly known as, 2, 4, 4'-trichloro-2-hydoxydiphenyl ether (0.2–0.5%)
4. N, N-Bis (Hydroxymethyl) urea (0.08–0.5%), Methyl p-Hydroxybenzoate (0.009–0.5%), Propyl p-Hydroxy benzoate (0.0025–0.5%), 1, 2-Propane diol (0.050–0.056%),
5. Coco Phosphotidyl PG-Dimonium chloride (0.05–0.5%)
6. DL- and L-Ofloxacin (0.01–0.5%)
7. Australian Tea Tree oil (1.0–5.0%)
8. Lemongrass oil (1.0–5.0%)
9. Thyme oil (1.0–5.0%)
10. Lavender oil (1.0–5.0%)
11. Clove oil (1.0–5.0%)

The antimicrobial compositions of the present invention are effective in controlling microorganisms when an effective amount of the composition is topically applied to a substrate or location, such as the hands, acne sites, injection sites, or site for catheters, etc. The amount applied to be effective depends upon such environmental factors as the length of application, the amount of contact of the antimicrobial composition and the substrate, as well temperature and evaporation rates. Those with skill in the art will readily be able to determine the effective level necessary to control the microorganisms. Typically, from about 0.5 to about 10 milliliters, preferably from about 1.0 to about 8, and most preferably from about 2.5 to about 5 milliliters of the antimicrobial composition is applied. This amount of the antimicrobial composition is found to be effective, to provide a logio reduction of 2 or more in the microbe population.

The present invention can also be prepared as an emulsion using techniques well known in the art, see for example U.S. Pat. No. 5,308,890. The active ingredients, excipients, etc., may be emulsified with an anionic, cationic, or nonionic surfactant or dispersing agent, or compatible mixtures thereof such as a mixture of an anionic or a nonionic surfactant, using, for example, from about 0.05% to about 5% by weight of a surfactant or dispersing agent based on the weight of the ingredients to be emulsified. Suitable cationic dispersion agents include lauryl pyridinium chloride, cetyldimethyl amine acetate, and alkyldimethylbenzylammonium chloride, in which the alkyl group has from 8 to 18 carbon atoms. Suitable anionic dispersing agents include, for example, alkali fatty alcohol sulfates, such as sodium lauryl sulfate, and the like; arylalkyl sulfonates, and the like; alkali alkyl sulfosuccinates, such as sodium octyl sulfosuccinate, and the like; and alkali arylalkylpolyethoxyethanol sulfates or sulfonates, such as sodium octylphenoxypolyethoxyethyl sulfate, having 1 to 5 oxyethylene units, and the like. Suitable non-ionic dispersing agents include, for example, alkyl phenoxypolyethoxy ethanols having alkyl groups from about 7 to 18 carbon atoms and from about 6 to about 60 oxyethylene units such as, for example, heptyl phenoxypolyethoxyethanols, ethylene oxide derivatives of long chained carboxylic acids such as lauric acid, myristic acid, palmitic acid, oleic acid, and the like, or mixtures of acids such as those found in tall oil containing from about 6 to 60 oxyethylene units; ethylene oxide condensates of long chained alcohols such as octyl, decyl, lauryl, or cetyl alcohols containing from 6 to 60 oxyethylene units; ethylene oxide condensates of long-chain or branched chain amines such as dodecyl amine, hexadecyl amine, and octadecyl amine, containing from about 6 to 60 oxyethylene units; and block copolymers of ethylene oxide sections combined with one or more hydrophobic propylene oxide sections. High molecular weight polymers such as hydroxyethyl cellulose, methyl cellulose, polyacrylic acid, polyvinyl alcohol, and the like, may be used as emulsion stabilizers and protective colloids.

The following examples are illustrative of the present invention and are not intended to limit the invention to the following compositions. Unless noted to the contrary, all percentages presented in this application are understood to be weight percent.

The following compositions were used in this application:
AMP 95 is a mixture of 2-amino-2-methyl-1-propanol, 2-(methylamino)-2-methyl-1-propanol and water in a ratio of from about 90:5:5, commercially available from Angus Chemical Company.
ACRITAMER® 505E, a polyvinyl carboxy polymer crosslinked with ethers of pentaerythritol, R.I.T.A. available from Crystal Lake, Ill.
ESS 9090IC is a fragrance, available from Givudan-Roure Corporation
CERAPHYL 28 is primarily cetyl lactate, a waxy solid commercially available from ISP Van Dyk Inc.
CERAPHYL 41 is a mixture of $C_{12}$–$C_{15}$ alcohol lactates, available from ISP Van Dyk Inc.
DOW CORNING® 580 wax is a mixture of stearoxy trimethoxy silane and stearyl alcohol.
GERMABEN II is a mixture comprised of diazolindinyl urea (about 30%); methyl paraben (about 11%); propyl paraben (about 3%) and propylene glycol (about 56%), available from Sutton Laboratories.
GERMALL PLUS. is a mixture of diazolidinyl urea (about 99%), 3-Iodo-propynylbutylcarbamate available from Sutton Laboratories.
LEXOREZ 100 is a saturated crosslinked hydroxy functional; polyester, comprised of glycerin, diethylene glycol, adipate crosslinked polymer, which is a viscous, hydrophobic liquid at room temperature and is dispersible in many lipids and emollients.
PHOSPOLIPID CDM is cocophosphatidyl (PG)-dimonium chloride, a co-synthetic, phospholipid available from Mona Industries, Inc.
PHOSPOLIPID PTC is cocamidopropyl phosphatidyl PG-dimonium chloride, available from Mona Industries.
SEAFOAM FRAGRANCE is a mixture of volatile compounds; available from Firmenich.
SILSOFT PEDM phenylethyl dimethicone, available from Witco Corporation, Osi Specialties, Inc.
TRICLOSAN - 2, 4, 4'-trichloro-2-hydoxydiphenyl ether.
ULTREZ® 10 a carbomer polymer, available from BF Goodrich, Cleveland Ohio, and disclosed in U.S. Pat. No. 5,004,598, the contents of which are incorporated by reference in its entirety.

EXAMPLE 1

The following formulations were prepared and tested, and the results are presented below:
Formulation 1: Ethyl alcohol 75.8; ULTREZ 10 0.6; glycerin 1.5; LEXOREZ 100 0.25; CERAPHYL-41 0.5; CERAPHYL-28 0.5; triclosan 0.3; AMP-95 pH 6.4; ESS 9090IC 0.06; cyclomethicone (245) 1.5; dimethicone (225) 0.5; Dow Corning 580 wax 0.20; SILSOFT PEDM 1.0; deionized water 17.6; PHOSPOLIPID CDM 0.2.
Formulation 2: Ethyl alcohol 50.0; Iso-propyl alcohol 20; ULTREZ 10 0.6; glycerin 1.5; LEXOREZ 100 0.25; CERAPHYL-41 0.5; CERAPHYL-28 0.5; triclosan 0.3; AMP-95 pH 6.4; ESS 9090IC 0.06; cyclomethicone (245) 1.0; dimethicone (225) 0.5; Dow Corning 580 wax 0.25; SILSOFT PEDM 1.0; deionized water 23.5; PHOSPOLIPID CDM 0.2.
Formulation 3: Ethyl alcohol 43.3; Iso-propyl alcohol 25; n-propyl alcohol 5.0; ULTREZ 10 0.6; glycerin 1.5; LEXOREZ 100 0.25; CERAPHYL-41 0.5; CERAPHYL-28 0.5; triclosan 0.3; AMP pH 6.4; ESS 9090IC 0.06; cyclomethicone (245) 2.0; dimethicone (225) 0.5; Dow Corning 580 wax 0.1; SILSOFT PEDM 1.0; deionized water 19.0; PHOSPOLIPID CDM 0.2; Phenoxy ethanol 0.2.
Formulation 4: Ethyl alcohol 75.8; ULTREZ 10 0.6; glycerin 1.5; LEXOREZ 100 0.25; CERAPHYL-41 0.5; CERAPHYL-28 0.5; triclosan 0.3; AMP-95 pH 6.4; ESS 9090IC 0.06; cyclomethicone (245) 1.0; dimethicone (225) 0.5; Dow Corning 580 wax 0.25; SILSOFT PEDM 1.0; deionized water 17.5; PHOSPOLIPID CDM 0.2; GERMABEN-II 0.05; preservatives 0.15
Formulation 5: Ethyl alcohol 75.8; ULTREZ 10 0.6; glycerin 1.5; LEXOREZ 100 0.25; CERAPAYL-41 0.5; CERAPHYL-28 0.5; benzethonium chloride 0.2; AMP-95 pH 6.4; ESS 9090IC 0.06; cyclomethicone (245) 1.0; dimethicone (225) 0.5; Dow Corning 580 wax 0.25; SILSOFT PEDM 1.0; deionized water 17.1; PHOSPOLIPID CDM 0.2.
Formulation 6: Ethyl alcohol 50; iso-propyl alcohol 20; ULTREZ 10 0.6; glycerin 1.5; LEXOREZ 100 0.25; CERAPHYL-41 0.5; CERAPHYL-28 0.5; 2, 4, 4-trichloro-2-hydoxydiphenyl ether 0.3; AMP-95 pH 6.4; ESS 9090IC 0.06; cyclomethicone (245) 1; dimethicone (225) 0.5; Dow Corning 580 wax 0.25; SILSOFT® PEDM 1.0; deionized water 23.0; PHOSPHOLIPID CDM 0.2; GERMABEN II 0.2; Disodium ethylenediaminetetraacetic acid (EDTA) 0.1.
Formulation 7: Ethyl alcohol 75.8; ULTREZ 10 0.6; glycerin 1.5; CERAPHYL-41 0.5; CERAPHYL-28 0.5; AMP-95 pH 6.4; ESS 9090IC 0.06; cyclomethicone (Dow Corning 245 fluid) 1.5; dimethicone (Dow Corning 225 fluid) 0.5; Dow Corning 580 wax 0.1; SILSOFT® PEDM 1.0; 2,4,4'-trichloro-2-hydoxydiphenyl ether 0.3; DL-Ofloxacin 0.05; deionized water 17.4.
Formulation 8: Ethyl alcohol 75.8; ULTREZ 10 0.6; glycerin 1.5; LEXOREZ 100 0.25; CERAPHYL-41 0.5; CERAPHYL-28 0.5; AMP-95 pH 6.4; ESS 9090IC 0.06; cyclomethicone (245) 1.5; dimethicone (Dow Corning 225) 0.5; Dow Corning 580 wax 0.1; SILSOFT PEDM 1.0; DL-Ofloxacin 0.25; deionized water 17.4.
Formulation 9: Ethyl alcohol 75.8; glycerin 1; 2, 4, 4'-trichloro-2-hydoxydiphenyl ether 0.3; ESS 9090IC 0.06; Triethanolamine, (pH adjuster), dimethicone (225) 1.0; Australian tea tree oil 1.5; deionized water 19.4; ACRITAMER 505E 0.45; PEG-75 Lanolin 0.5; Lavender oil 1.5.
Formulation 10: Ethyl alcohol 75.8; glycerin 1; 2, 4, 4'-trichloro-2-hydoxydiphenyl ether 0.3; ESS 9090IC 0.06; Triethanolamine (pH adjuster), dimethicone (225) 1; deionized water 19.4; ACRITAMER 505E 0.45; PEG-75 Lanolin 0.5; Lavender oil 1.5.
Formulation 11: Ethyl alcohol 75.8; glycerin 1; 2, 4, 4'-trichloro-2-hydoxydiphenyl ether 0.3; ESS 90901IC 0.06; Triethanolamine (pH adjuster), dimethicone (225) 1; deionized water 19.4; ACRITAMER 505E 0.45; PEG-75 Lanolin 0.5; Lemon Grass Oil 1.0.
Formulation 12: Ethyl alcohol 75.8; glycerin 1; 2, 4, 4'-trichloro-2-hydoxydiphenyl ether 0.3; ESS 9090IC 0.06; Triethanolamine (pH adjuster), dimethicone (225) 1; deionized water 19.4; ACRITAMER 505E 0.45; PEG-75 Lanolin 0.5; Thyme Oil 1.0.
Formulation 13: Ethyl alcohol 75.8; glycerin 1; 2, 4, 4'-trichloro-2-hydoxydiphenyl ether 0.3; ESS 9090IC 0.06; Triethanolamine (pH adjuster), dimethicone (225) 1; deionized water 19.4; ACRITAMER 505E 0.45; PEG-75 Lanolin 0.5; Clove Oil 1.0.

The antimicrobial formulations were evaluated for their ex-vivo clinical efficacy, and the test results of the compositions are summarized in Tables 1, 2 and 3.

A pig skin test model was used as a protocol to evaluate or screen a number of sample antimicrobial compositions.

Because pig skin is similar to human skin in terms of skin components and behavior, pig skin is suitable to simulate hand washing techniques that are clinically performed by humans. The test is modeled after the test outlined in Pig Skin as Test Substrate for Evaluating Topical Antimicrobial Activity, J. Clin. Microbiology, Sept., 1986, p.343–348.

The pig skin test consisted of: a) preparation of the pig skin; b) antimicrobial ' challenge; and c) enumeration with controls.

The pig hide was washed and dehaired and then frozen. The pieces are then thawed and cut into 3×3 cm sections. The skin was mounted to a holder with an epoxy with the skin side exposed. The skin pieces were place into Petri dishes containing a filter disk moistened with 1.0 ml of water to prevent drying. The skins were placed in a refrigerator overnight.

On the same day that the skin was prepared, the test organism was inoculated on standard methods agar slants and standard methods agar plates in duplicate. The sectioned pig skin was tested for the presence of residual antibiotics by randomly cutting plugs (8 mm biopsy plug) from the hide and placing the plug skin side down into individual agar plates seeded with the test organism. On the following day, plates were examined for a zone of inhibition surrounding the pig skin. An inhibition zone is indicative of residual antibiotics and the skin was not used.

Suspensions of the various organisms were made from overnight slant cultures. Cultures were suspended with 10 ml of Butterfield buffer by gently rubbing the surface with agar with a sterile cotton swab. The suspensions were mixed together to provide a mixed inoculum of approximately $10^9$ CFU/ml. The titer of organisms was further diluted to yield approximately $10^7$ CFU/ml. Two pieces of pig skin were inoculated with 0.05 ml of diluted culture. Each pair of inoculated skin was paired with an un-inoculated skin. The pair inoculated and un-inoculated skin were rubbed together for approximately 15 seconds and incubated for approximately 15 minutes at 30° C. with the cover removed to allow the organisms to dry onto the skin. After incubation, 0.50 ml of test material was added to the pieces of skin from each pair. Incubation was done at room temperature with the Petri dish cover removed. One paired duplicate from each set was enumerated through imprinting onto an agar plate while the other duplicate was enumerated by rinsing.

Imprints were made by inverting the mounting holder and pressing the treated skin onto the surface of standard methods agar with lecithin and polysorbate 80. Imprints were made at specified time intervals and then incubated at approximately 30° C. for about 24 hours.

At each time interval, 0.2 ml of letheen thioglycolate neutralizing broth was added to the surface of the pair of skin from the pair. The resulting 10 ml wash from using both pieces of skin was collected and used to enumerate the surviving organisms. Aliquots (0.5 ml) of wash broth were serially diluted to extinction in 4.5 ml of letheen thioglycolate neutralizing broth. Plates were incubated at 30° C. for approximately 48 hours and then counted.

The results are presented below:

TABLE 1

Pig Skin test results with a Mixed Culture*

| Formulation | Inoculum Controls (BL) ($Log_{10}$) | $Log_{10}$ Reductions | | |
|---|---|---|---|---|
| | | 15 min. | 60 min. | 120 min. |
| 1 | 7.42 | 1.8 | 2.48 | 1.85 |
| 2 | 5.84 | 1.1 | 2.7 | 2.38 |
| 3 | 7.24 | 1.7 | 2.65 | 0.83 |
| 4 | 7.42 | 1.78 | 1.76 | 3.76 |
| 5 | 5.84 | 4.1 | 2.8 | 2.17 |
| 6 | 5.84 | 3.55 | 2.65 | 2.10 |
| 7 | 5.84 | 3.82 | 3.38 | 3.61 |
| 8 | 5.84 | 4.14 | 3.94 | 4.44 |
| HIBISTAT | 5.84 | 3.0 | 3.3 | 0.62 |

*Mixed Culture with each of the cultured materials equally represented:
*Pseudomonas aeruginosa* ATCC 15442,
*Klebsiela pneumoniae* ATCC 11296,
*Micrococcus luteus* ATCC 7468,
*Enterococcus faecalis* ATCC 29212

Those with skill in the art will appreciate that the compositions with higher $log_{10}$ reduction value indicates improved efficacy. The $log_{10}$ reduction is the difference in the initial bacterial counts and the count recovered after each treatment.

The same formulations were tested on Pig Skin test results on *Staphylococcus aureus* ATCC 33592. The results, reported with time reported in minutes, are presented in Table 2 below:

TABLE 2

| Formulation | Inoculum Controls (BL) ($Log_{10}$) | $Log_{10}$ Reductions | | |
|---|---|---|---|---|
| | | 15 min. | 60 min. | 120 min. |
| 1 | 7.55 | 2.28 | 2.06 | 1.98 |
| 2 | 4.99 | 1.37 | 1.88 | 0.03 |
| 3 | 7.55 | 2.45 | 3.04 | 2.54 |
| 4 | 7.55 | 4.2 | 2.22 | 1.8 |
| 5 | 4.99 | 1.74 | 1.96 | 2.19 |
| 6 | 4.99 | 0.15 | 2.23 | 2.18 |
| 7 | 4.99 | 2.58 | 2.83 | 3.14 |
| 8 | 4.99 | 2.84 | 2.65 | 2.86 |
| HIBISTAT | 4.99 | 2.45 | 1.54 | 0.85 |

The results in Table 2 indicate that excellent bactericidal activity was obtained against *Staphylococcus aureus* using the iso-propyl alcohol formulations.

The same formulations were tested using Pig Skin test protocol on *Serratia marcescens* ATCC 14756. The results are presented in Table 3 below:

TABLE 3

| Formulation | Inoculum Controls (BL) ($Log_{10}$) | $Log_{10}$ Reductions | | |
|---|---|---|---|---|
| | | 15 min. | 60 min. | 120 min. |
| 1 | 7.01 | 1.93 | 1.25 | 1.04 |
| 2 | 5.17 | 2.32 | 0.96 | 0.4 |
| 3 | 7.01 | 2.1 | 1.77 | 1.10 |
| 4 | 7.01 | 3.53 | 3.07 | 0.77 |
| 5 | 5.17 | 2.64 | 1.64 | 1.48 |

TABLE 3-continued

| Formulation | Inoculum Controls (BL) ($Log_{10}$) | $Log_{10}$ Reductions | | |
|---|---|---|---|---|
| | | 15 min. | 60 min. | 120 min. |
| 6 | 5.17 | 3.32 | 2.18 | 0.32 |
| 7 | 5.17 | 2.18 | 3.29 | 2.26 |
| 8 | 5.17 | 3.52 | 2.9 | 1.63 |
| 9 | 7.04 | 2.12 | 3.08 | 2.78 |
| 10 | 7.04 | 4.52 | 3.51 | 2.96 |
| 11 | 7.04 | 3.76 | 3.89 | 2.89 |
| 12 | 7.04 | 3.23 | 3.36 | 3.31 |
| 13 | 7.04 | 4.11 | 3.89 | 1.93 |
| HIBISTAT | 5.17 | 2.08 | 2.06 | 0.03 |

Table 3 indicates that ethyl alcohol and isopropyl alcohol antimicrobial formulations containing essential oils, particularly Lemongrass oil, Lavender, Thyme, Australian tea tree oil and clove oil provided excellent activity against *Serratia marcescens* ATCC 14756.

EXAMPLE 2

Based upon the results found in Example 1 above, four formulations, (A–D) were prepared and were evaluated for their in-vivo efficacy following a modified Health Care Personnel Handwash protocol. The four formulations are as follows:
Formulation A: Ethyl alcohol (92.3% by weight) 75.8; ULTREZ® 10 0.6; glycerin 0.5; LEXOREZ® 100 0.25; CERAPHYL-41 0.5; CERAPHYL-28 0.5; triclosan (2, 4, 4-trichloro-2-hydoxydiphenyl ether) 0.3; phenoxy ethanol 0.3; benzalkonium chloride (50% solution) 0.2; PHOSPHOLIPID CDM 0.05; GERMALL PLUS+GERMABEN II (1:1 weight ratio) 0.2; Vitamin E linoleate 0.05; AMP pH 6.4; ESS 9090IC 0.06; deionized water 20.4.
Formulation B: Formulation B is substantially similar to Formulation A except no triclosan was employed. Ethyl alcohol 75.8; ULTREZ® 10 0.6; glycerin 0.5; LEXOREZ® 100 0.25; CERAPHYL-41 0.5; CERAPHYL-28 0.5; phenoxy ethanol 0.3; benzalkonium chloride (50% solution) 0.2; PHOSPOLIPID CDM 0.05; GERMALL PLUS+GERMABEN (1:1) 0.2; Vitamin E linoleate 0.05; AMP pH 6.4; ESS 9090IC 0.06; deionized water 20.5.
Formulation C: Ethyl alcohol 75.8; ULTREZ 10 0.6; glycerin 1.5; LEXOREZ 100 0.25; CERAPHYL 41 0.5; CERAPHYL 28 0.5; 2, 4,4'-trichloro-2-hydoxydiphenyl ether 0.3; phenoxyethanol 0.3; benzethonium chloride 0.1; benzalkonium chloride (50% solution) 0.1; PHOSPOLIPID CDM 0.05; GERMALL PLUS+GERMABEN (1:1) 0.2; Vitamin E linoleate 0.05; AMP pH 6.4; ESS 9090IC 0.06; cyclomethicone (245) 2.5; dimethicone (225) 0.5; Dow Corning 580 wax 0.1; SILSOFT PEDM 0.5; deionized water 15.8.
Formulation D: Ethyl alcohol 43.2; iso-propyl alcohol 25; n-propyl alcohol 5; ULTREZ 10 0.6; glycerin 1.5; LEXOREZ® 100 0.25; CERAPHYL-41 0.5; CERAPHYL-28 0.5; 2, 4, 4'-trichloro-2-hydoxydiphenyl ether 0.3; phenoxy ethanol 0.3; benzalkonium chloride (50% solution) 0.2; Vitamin E linoleate 0.025; AMP pH 6.4; ESS 9090IC 0.06; cyclomethicone (245) 3.5; dimethicone (225) 0.5; Dow Corning 580 wax 0.1; SILSOFT PEDM 0.5; lemon grass oil 2.5; Australian tea tree oil 2.5; deionized water 12.
These formulations were compared with commercially available chlorhexidine gluconate based products such as HIBISTAT and HIBICLENS, commercially available antimicrobials from ICI Americans.

TABLE 4

$Log_{10}$ Reductions from Baseline Using the Health Care Personnel Handwash Protocol

| Formulations | Base Line | Wash 1 | Wash 3 | Wash 7 | Wash 10 |
|---|---|---|---|---|---|
| A | 8.23 | 3.55 | 3.08 | 3.67 | 3.03 |
| B | 8.56 | 4.13 | 3.4 | 3.92 | 3.04 |
| C | 8.36 | 3.75 | 3.15 | 3.06 | 3.18 |
| D | 8.45 | 4.26 | 4.42 | 4.55 | 4.57 |
| HIBISTAT | 8.23 | 3.25 | 3.94 | 5.31 | 2.86 |
| HIBICLENS | 8.32 | 2.2 | 2.6 | 3.0 | 2.9 |

All four formulations from Example 1 met FDA requirements at wash 1, (a 2 $log_{10}$ reduction), and at wash 10, (a 3 $log_{10}$ reduction). Formulations A–D, were found to be more effective than the commercially available products. Alcohol and chlorhexidine gluconate combinations do show excellent build-up on 10 handwashes, but at the 10th wash, where a neutralizer is being used to quench the activity, a drop was noted in the log reduction value from the 7th wash ranging between 40 and 50%. Surprisingly, all four formulations of the present invention did not replicate this drop in efficacy.

EXAMPLE 3

Additional experimental formulations were prepared as emulsions, using the antimicrobial formulations described in Examples 1 and 2 above, with minor modifications. In total 8 samples were prepared out of which four test formulations were evaluated using an in-vitro bactericidal test against 8 representative microorganisms (gram negative, gram positive and fungus) at four time intervals, and two concentrations.
The formulations used in this Example are set forth below:
Formulation A': Water 80.32, Propylene Glycol 4, Myristyl Myristate 1.5, Oleic Acid 1.25, Stearic Acid 1.25, Glyceryl Stearate 1.25, Polysorbate 61 1.2, Isopropyl Palmitate 1, Dimethicone 1, Stearoxy trimethyl silane 1, Sorbitane Stearate 0.8, Cetyl Alcohol 0.5, Stearyl Alcohol 0.5, Synthetic Beeswax 0.5, Benzyl Alcohol 0.3, Carbomer 941 0.8, Fragrance IFF 1906AD 0.2, Disodium EDTA+NaOH 0.15+0.8, Phenoxy Ethanol 0.4, Lactic Acid 0.5, GERMABEN-II 0.25, Panthenol 0.2, Tocopheryl Acetate 0.05, Vitamin E Linoleate 0.05, Triclosan 0.3.
Formulation B': Water 80.32, Propylene Glycol 4, Myristyl Myristate 1.5, Oleic Acid 1.25, Stearic Acid 1.25, Glyceryl Stearate 1.25, Polysorbate 61 1.2, Isopropyl Palmitate 1, Dimethicone 1, Stearoxy trimethyl silane 1, Sorbitane Stearate 0.8, Cetyl Alcohol 0.5, Stearyl Alcohol 0.5, Synthetic Beeswax 0.5, Benzyl Alcohol 0.8, Carbomer 941 1.0, Fragrance IFF 1906AD 0.2, Disodium EDTA+NaOH 0.15+0.75, Phenoxy Ethanol 0.4, Lactic Acid 0.5, sodium hydroxy methyl glycinate (50% active) 0.3, GERMABEN-II 0.25, Benzethonium Chloride 0.2, Tocopheryl acetate 0.05, Vitamin E Linoleate 0.05, Phospholipid PTC+CDM (1:1) 1, Triclosan 0.3, GS-Liquorice 0.1.
Formulation C': Water 80.32, Propylene Glycol 4, Myristyl Myristate 1.5, Oleic Acid 1.25, Stearic Acid 1.25, Glyceryl Stearate 1.25, Polysorbate 61 1.2, Isopropyl Palmitate 1, Dimethicone 1, Stearoxy trimethyl silane 1, Sorbitane Stearate 0.8, Cetyl Alcohol 0.5, Stearyl Alcohol 0.5, Synthetic Beeswax 0.5, Benzyl Alcohol 0.3, Carbomer 941 0.8, Fragrance IFF 1906AD 0.2, Disodium EDTA+NaOH 0.15+0.75, Phenoxy Ethanol 0.4, Lactic Acid 0.5, GERMALL Plus 0.3, GERMABEN-II 0.25, Benzalkonium Chloride (50%) 0.2, Tocopheryl acetate 0.05, Vitamin E Linoleate 0.05, PHOSPHOLIPID PTC+CDM (1:1) 1, Triclosan 0.3.

Formulation D': Water 80.32, Propylene Glycol 4, Myristyl Myristate 1.5, Oleic Acid 1.25, Stearic Acid 1.25, Glyceryl Stearate 1.25, Polysorbate 61 1.2, Isopropyl Palmitate 1, Dimethicone 1, Stearoxy trimethyl silane 1, Sorbitane Stearate 0.8, Cetyl Alcohol 0.5, Stearyl Alcohol 0.5, Synthetic Beeswax 0.5, Benzyl Alcohol 0.3, Carbomer 941 0.8, Fragrance IFF 1906AD 0.2, Disodium EDTA+NaOH 0.15+ 0.75, Phenoxy Ethanol 0.4, Lactic Acid 0.5, octanoyl collagenic acid 0.3, GERMABEN-II 0.25, Cetyl pyridinium chloride 0.2, Tocopheryl Acetate 0.05, Vitamin E Linoleate 0.05, PHOSPHOLIPID PTC+CDM (1:1) 1, Tricoslan 0.3.

TABLE 5

In-vitro bactericidal activity of emulsions

| Microorganism | ATCC | Time* for >99.99% Kill | | | |
|---|---|---|---|---|---|
| | | A' | B' | C' | D' |
| Enterococcus faecalis (MDR) | 51299 | 60 | 60 | 15 | 15 |
| Staphylococcus aureus (MRSA) | 33592 | 60 | 60 | 15 | 60 sec. |
| Staphylococcus aureus | 6538 | 60 | 60 | 15 | 15 |
| Serratia marcescens | 14756 | >60 | 60 | 15 | 60 sec. |
| Streptococcus pneumoniae | 6303 | 15 | 15 | 15 | 30 sec. |
| Escherichia coli | 11229 | 15 | 15 | 30 sec. | 30 sec. |
| Pseudomonas aeruginosa | 15442 | 30 sec. | 30 sec. | 30 sec. | 30 sec. |
| Candida albicans | 10231 | all results more than 60 | | | |

All times reported in minutes unless noted otherwise; sec. is understood to be seconds.

The above data indicates the superior efficacy that Formulation D' has in killing both the gram positive and gram negative bacteria indicated above.

The antimicrobial mixture of the present invention has shown comparable activity when formulated in non-aqueous base, i.e., when made into an emulsion. Formulation D' displayed promising results particularly against *Staphylococcus aureus* (MRSA) and *Serratia marcescens* (ATTC 14756). Most triclosan-containing antimicrobial formulations have limited activity against *Serratia marcescens* (ATTC 14756). The antimicrobial compositions of the present invention, and in particular formulation D', have potential application in topical skin care products, like alcohol gels, creams, lotions, scrubs, pre-operative preparations, cleansers, ointments, therapeutics and other applications against disease causing pathogens.

EXAMPLE 4

Compositions of the present invention were tested for irritation and sensitivity. The following formulations were prepared:

Formulation 1: deionized water 28.7, ethyl alcohol 62, ULTREZ® 10 0.45, glycerin 0.5, cyclomethicone 1.25, Dow Corning® 580 Wax 0.025, SILSOFT® PEDM 0.2, CERAPHYL®-28 0.5, CERAPHYL®-41 1.0, AMP 95 (pH adjuster) as needed, 1906 AD MOD I 0.1.

Formulation 2: deionized water 27.7, ethyl alcohol 62, ULTREZ 10 0.55, glycerin 0.5, cyclomethicone 1.25, Dow Corning 580 Wax 0.025, SILSOFT® PEDM 0.2, CERAPHYL®-28 0.5, CERAPHYL®-41 1.0, AMP 95 (pH adjuster) as needed, 1906 AD MOD I 0.06, phenoxy ethanol 0.5, benzalkonium chloride (50% active) 0.16, benzethonium chloride 0.08, PHOSPHOLIPID CDM 0.05, GERMALL PLUS. 0.1, GERMABEN II 0.1.

Prior to study the subjects were screened to assure that they met the inclusion/exclusion criteria. Each subject was provided with a schedule of the study activities. The Induction Phase consisted of nine (9) consecutive applications of the study material and subsequent evaluations of the study sites were assessed. Prior to the applications of the patches, the sites were outlined with a skin marker, e.g., gentian violet. The subjects were required to remove the patches approximately 24 hours after application. The subjects returned to the facility at 48 hour intervals to have the sites evaluated and identical patches reapplied. Following the ninth evaluation, the subjects were dismissed for a 10–14 day rest period. After the rest period, the challenge period was initiated during the 6th week of the study with the identical patches applied to the sites previously unexposed to the study. These patches were removed by subjects after 24 hours and the sites graded after additional 24-hour and 48 hour periods. The gradings were done 48 and 72 hours after application. To be considered a completed case, a subject must have nine (9) applications and no less than eight (8) subsequent readings during induction and one (1) product application and two (2) readings during the challenge. Of the 101 subjects that completed the study, there was no evidence of sensitization or irritation due to the formulations.

EXAMPLE 6

The two formulations employed in Example 5 above were investigated to determine their moisturizing capabilities. Fifteen subjects applied the formulations to the dry skin on the lateral aspect of the lower leg. The moisturization of the skin was measured using the SKICON® Skin Surface Hydrometer. All results are reported as mean percent changes from baseline in SKICON measurements. As used herein mean percent results were found by compared by measuring the moisturization values at four different sites and comparing the mean value of moisturization for the four sites with baseline values.

| | 30 Minutes | 1 Hour | 2 Hours |
|---|---|---|---|
| Formulation 1 | 4.6% | 16.7% | 19.9% |
| Formulation 2 | 5.5% | 18.8% | 23.3% |
| Untreated control | 16.5% | 35.3% | 39.7% |

The results indicated that both Formulations 1 and 2 behaved similarly when compared with the and were superior to the untreated control. This indicates that the formulations were non-drying. Both formulations were surprising in that for formulations containing high levels of alcohol the products were not found to posses significant drying effects.

EXAMPLE 7

The following product formulation was prepared and tested in order to evaluate the antimicrobial properties using different microbiological strains: deionized water 27.8; ethyl alcohol 62.0 by volume; ULTREZ 10 0.55; glycerin 0.5; cyclomethicone (245) 1.25; Dow Corning 580 wax 0.025; SILSOFT PEDM 0.2; CERAPHYL-28 0.5; CERAPHYL-41 1.0; phenoxyethanol 0.5; benzalkonium chloride (50% active) 0.2; PHOSPHOLIPID CDM 0.05; GERMALL PLUS. 0.1; GERMABEN II 0.1; 1906-AD Mod I 0.06 and pH adjuster.

The antimicrobial properties of the formulation was evaluated a concentration of 99% (w/v), using exposure of fifteen seconds, thirty seconds, and one minute. The samples were prepared using a 0.1 ml aliquot of challenge suspension of approximately 1.0×10⁹ CFU/ml and were added to 9.9 ml of product and mixed thoroughly to achieve a 99% (w/v) concentration. The 15 second, 30 second and one minute exposures were timed with a calibrated minute/second timer.

0.1 ml of each challenge suspension was placed into a sterile test tube containing 9.9 ml of Butterfield's Phosphate Buffer solution. This solution was used as a control. Appropriate ten-fold dilutions were made with Butterfield's Phosphate Buffer solution. After incubation, approximately 1–2 days at 35° C., the colonies on the plates were counted using a hand-tally counter. The $\log_{10}$ values of the plates were compared to the initial population. It is understood that the numbers reported below as 10+7 is $10^7$. The results are as follows:

The formulation demonstrates excellent antimicrobial activity, 99% reduction against all of the listed organisms. The above organisms include a broad spectrum of organisms, including gram negative, gram positive, and fungi microbes.

EXAMPLE 8

Subjects were instructed not to use any anti-microbial and or antiseptic articles, with the exception of the test articles. Petri dishes were filled with approximately 11.5 ml of sterilized molten soybean casein digest agar. The agar was allowed to solidify and was placed in an incubator at 35° C. overnight prior to inoculation. The test bacteria were grown in trypticase soy broth and diluted to obtain approximately 200–300 colony forming units (CFU) per 10 microliters. A 10 microliter loop was used to deliver 10 microliter of the final dilution onto the covered surface of each agar plate and spread using the loop. The plates were allowed to dry inside the Petri dishes for 15–30 minutes before application to the subject arms. Prior to application to the subject's arms 70% iso-propyl alcohol was used for about 10 seconds to reduce the possibility of contamination. A technician applied about 2.5 ml of the test solution over the volar surface of the subject's arm. The subject then spread the solution from wrist to elbow until the test article disappeared.

After applying and air drying, the subjects were challenged with the anti-microbial solution either immediately (within 5 minutes of treatment), 1 hour, 3 hours 5 or 8 hours post treatment. The antimicrobial solutions used were a commercially available 62% by volume ethyl alcohol (designated as A) and the formulation used in Example 7 above (designated as B).

The results were as follows:

| Treatment: Time of Exposure | Untreated Sites* | Treated Sites* |
|---|---|---|
| B-8 Hours | 77 | 83 |
| | 118 | 125 |
| | 64 | 71 |
| | 103 | 115 |
| | 88 | 111 |
| | 107 | 97 |
| Average for Group B-5 hours | 92.8 | 100 |
| | 124 | 125 |
| | 84 | 83 |
| | 135 | 89 |
| | 67 | 93 |
| | 87 | 21 |
| | 134 | 40 |
| Average for Group B-3 hours | 105 | 76 |
| | 132 | 6 |
| | 87 | 0 |
| | 127 | 3 |
| | 107 | 10 |
| | 153 | 86 |
| | 113 | 48 |
| Average for Group B-1 hour | 120 | 26 |
| | 79 | 63 |
| | 100 | 5 |
| | 68 | 81 |
| | 71 | 2 |
| | 127 | 10 |
| | 118 | 0 |
| Average for Group A-1 hour | 94 | 27 |
| | 139 | 169 |
| | 130 | 136 |
| | 121 | 164 |
| | 137 | 167 |
| | 98 | 135 |
| | 99 | 117 |
| Average for Group B-5 minutes | 121 | 148 |
| | 94 | 0 |
| | 142 | 1 |
| | 116 | 2 |
| | 86 | 0 |
| | 95 | 0 |
| | 91 | 0 |
| Average for Group | 104 | 0.5 |

*Colony Forming Units (CFU)

The above data indicates that the present invention was very effective in killing germs at 5 minutes and also had very effective residual activity after 3 hours in preventing microbial growth.

EXAMPLE 9

Listed below are typical ranges for components of the present invention and the synergistic combinations for exhibition of excellent antimicrobial activity with staining properties.

| INGREDIENTS | PERCENTAGE BY WEIGHT |
|---|---|
| Deionized water | 20–40 |
| Alcohol (Percent by volume) | 60–70 |
| Glycerin | 0.1–10 |
| Cationic antimicrobials (e.g., benzalkonium chloride, cetyl pyridinium chloride, polyhexamethylene biguanide) | 0.05–0.5 |
| Complexing agents (Na2EDTA) | 0.01–0.1 |
| Carbomer Polymer such as ULTREZ 10 | 0.2–2.0 |
| Naturally derived phospholipids (e.g., Phospholipid CDM, PTC) | 0.01–2.0 |
| Phenylethyl dimethicone (Silsoft PEDM) | 0.01–2.0 |
| Dow wax | 0.01–1.00 |
| Cyclomethicone | 0.5–5.0 |
| Cetyl lactate and C12—C15 alkyl lactate | 0.1–2.00 |
| Curcuma longa | 0.5–10 |
| Hydrastis canadensis | 0.5–10 |
| Croccus sativus (Saffron) and Alkanna tinctoria (Henna root) | 0.5–10 |

-continued

| INGREDIENTS | PERCENTAGE BY WEIGHT |
|---|---|
| Phenoxyethanol | 0.1–1.0 |
| Germall Plus | 0.01–0.5 |
| Germaben-II | 0.1–1.0 |

Antimicrobial Hand Gel Composition A was prepared and tested by following the method for skin prep outlined below. The hand gel was comprised of the following ingredients based on percent (W/V) except as noted:

| ANTIMICROBIAL HAND GEL COMPOSITION A | | |
|---|---|---|
| Material | Percent (W/V) | Percent (W/W) |
| Specially Denatured Alcohol 40B, 200 Proof (density = 0.7872 g/mL @ 22.3° C.) | 47.76 (60.6 (v/v) | 57.39 |
| Purified Water (USP) (adjustable) | 36.85 | 40.09 |
| Cyclomethicone (Dow Corning ® 245 Fluid) | 1.5 | 1.66 |
| Ceraphyl ® 41 | 1.0 | 1.11 |
| Ceraphyl ® 28 | 0.5 | 0.56 |
| Glycerin, 99% (USP) | 0.5 | 0.56 |
| Phenoxyethanol (Dowanol ® EPH Glycol Ether) | 0.5 | 0.56 |
| Carbomer (Carbopol Ultrez 10) | 0.45 | 0.50 |
| Silsoft ® PEDM Organosilicone Fluid | 0.2 | 0.22 |
| AMP-95 ® (pH adjuster) | 0.15 | 0.19 |
| Seafoam 143258 G Fragrance | 0.12 | 0.13 |
| Propylene Glycol (USP) | 0.1 | 0.11 |
| Germall ® Plus | 0.1 | 0.11 |
| Germaben ® II | 0.1 | 0.11 |
| Benzalkonium Chloride, 50% Solution (USP/NF) | 0.2 | 0.22 |
| Phospholipid CDM | 0.05 | 0.05 |
| Stearoxymethylsilane (Dow Corning ® 580 Wax) | 0.025 | 0.03 |
| Total | 90.105% (W/V) | 100.00 (W/W) |

The FDA issued a tentative final monograph (Federal Register, Vol.59, pp. 31402 to 31452, Jun. 17, 1994) describing a procedure to demonstrate the antimicrobial efficacy of products intended for use as patient preoperative skin preparations. The procedure is a modification of ASTM E-1173-93. Activity of the pre-operative skin preparation is measured by comparing microbial counts obtained at various time intervals after application of the pre-operative treatment to skin sites located on the abdomen and in the groin to counts obtained from the same sites prior to treatment application.

The FDA proposed performance criteria requires that skin prepped with a formulation show atleast 2-log reduction in the bacterial flora on abdominal skin sites and atleast 3-log reduction in the flora of groin sites 10 minutes after prepping. Additionally the proposed monograph indicates that six hours after product use the bacterial count from both sites must remain below baseline.

This test method is conducted on subjects selected from a group of volunteers who, after refraining from using topical and oral antimicrobials for at least two weeks, exhibit high skin flora counts on the abdomen and groin.

This study is within-subjects, paired comparison of two antimicrobial products. Bacterial reduction at 10 minutes and 6 hours was determined on abdominal and groin sites.

In total 11 groin sites and 11 abdomen site with antimicrobial hand gel and 11 groin sites and 11 abdominal site with Betadine surgical scrub was evaluated using a 5-minute application procedure. Additionally, 4 groin sites and 4 abdominal sites were prepped with antimicrobial hand gel using a 30-second application procedure.

| | | $LOG_{10}$ REDUCTIONS | | | |
|---|---|---|---|---|---|
| TEST PRO- | | 10 MINUTE EVALUATION | | 6 HOUR EVALUATION | |
| DUCT | TREATMENT | ABDOMEN | GROIN | ABDOMEN | GROIN |
| A | 5 MINUTES | 2.29 | 3.12 | 1.94 | 2.64 |
| B | 5 MINUTES | 1.84 | 1.15 | 2.19 | 1.99 |
| A | 30 SECONDS | 2.77 | 2.04 | 1.47 | 2.03 |

A: ANTIMICROBIAL HAND GEL
B: BETADINE 7.5% POVIDONE-IODINE

Interestingly Composition A met FDA 2 log (abdomen) and 3 log (Groin) reduction requirements after 10 minutes prepping, whereas, Composition B (Betadine) failed to meet these requirements. It is also quite surprising to note that comparing the results of Betadine at 5 minute treatment and antimicrobial hand gel at 30 seconds treatment, the gel has shown equivalent results to Betadine only after 30 seconds of treatment.

Also, it is interesting and surprising to note that Composition A exceeded the proposed FDA criteria for performance on both abdominal and groins sites when the 5-minute treatment procedure was employed. Using a 30-second treatment procedure, Composition A met the proposed efficacy criteria when applied to abdominal sites but didn't provide the required 3-log reduction after 10 minute prepping on groin sites. However, Composition B identified as Betadine surgical scrub, which was evaluated by the 5 minute treatment procedure only, failed to meet the proposed performance criteria for both the abdominal and groin sites.

The bacterial counts remained below the baseline for 6 hours and thus both products met the FDA requirements to qualify as a pre-operative product.

This data shows the strong antimicrobial activity and depositing features of the compositions of this invention.

EXAMPLE 10

Therapeutic Skin Shave

Composition A was used as a shaving gel, and found quite effective for the treatment of PFB. Eight subjects were part of this screening study. Each subject used the product for six weeks. After six weeks of the application, there was a significant decrease in the number of PFB lesions on both the left side and right side of the face as assessed clinically by the grader. A visual comparison of digital photographs between visit 1 and visit 3 showed clear improvement in three subjects. These test results clearly suggests the anti-inflammatory properties of the Composition A gel. At the end of the study subjects perceived an improvement in the appearance of their PFB/razor bumps. Thus, surprisingly Composition A has shown potential for the treatment of bacterial driven PFB.

EXAMPLE 11

Therapeutic Acne Application

A twelve-week study was conducted to assess the efficacy of an antimicrobial gel for the treatment of acne vulgaris.

Volunteer subjects were selected from a pool of healthy men and women ages 12–30. Subjects qualified for participation by having at least 15 inflammatory acne lesions (predominantly papules) on their face, no more than 5 pustules, and a Cook Acne Grading score of 2 to 4 (Cook, C H, Centner, R L, Michaels, S E. *An acne grading method using photographic standards* Arch. Dermatol. 1979. 115:571) Fourteen subjects completed this study.

At baseline, after three days of product use, and after one, four and twelve weeks of product use, subjects' faces were examined and graded for lesion erythema and lesion elevation (by palpation) on the forehead, cheeks and chin. Subjects also had inflammatory acne lesions (papules, pustules and nodules), non-inflammatory acne (open and closed comedones) and macules counted on the forehead, cheeks and chin. Subjects completed self-assessment questionnaires at each visit after baseline, and completed a post-usage questionnaire at the last visit (twelve weeks).

After just three days of treatment a significant reduction in papules was observed for the chin region. After 1 week, 4 weeks and 12 weeks, a significant reduction in papules was observed over the whole face when compared to baseline. Moreover, by 12 weeks, a significant reduction in closed comedones was also observed, which indicates that the test product not only significantly reduces inflammatory acne, but also significantly reduces closed comedones which are believed to be the pre-cursor lesion to inflammatory papules (Burke, B M, Cunliffe, W J. *The assessment of acne vulgaris: the Leeds technique* Br. J. Dermatol. 1984. 111:83). Moreover, the average percent improvement from baseline in inflammatory papules was 16% at Day 3, 35% at 1 week, 39% at 4 weeks and 53% at 12 weeks. The degree of improvement observed during this study compares very favorably with the comparative effects of 10% benzoyl peroxide, and 10% benzoyl peroxide in combination with 3% topical erythromycin. Sklar et al. (Sklar, J L, Jacobson, C, Rizer, R L, Gans, E H. *Evaluation of Triaz 10% Gel and Benzamycin in acne vulgaris* J. Dermatological Treatment. 1996. 7:147) observed that 10% benzoyl peroxide reduced papules and pustules by 16% at 1 week, 43% at 4 weeks, and 56% at 12 weeks of treatment compared to baseline. In addition they showed that the combination of 10% benzoyl peroxide and 3% topical erythromycin reduced papules and pustules an average of 24% at 1 week, 43% at 4 weeks and 54% at 12 weeks. Their data compares very favorably with the results obtained with the present study with treatment effectiveness essentially comparable. Thus, antimicrobial Composition A proved to be effective in treatment of acne.

What is claimed is:

1. An antimicrobial composition comprising:
    a) an antimicrobial selected from the group consisting of greater than 30% by volume alcohol, an effective amount of triclosan and mixtures thereof; and
    b) an effective amount of phenoxy ethanol, benzalkonium chloride or benzethonium chloride, and cocophosphatidyl-dimonium chloride; and
    c) an effective amount of naturally occurring plant or plant extract.

2. The composition of claim 1 wherein the alcohol is selected from the group consisting of ethyl alcohol, isopropyl alcohol and n-propyl alcohol and mixtures thereof.

3. The composition of claim 1 wherein the phenoxy ethanol is from about 0.25 to about 5.0 percent by weight; the benzalkonium chloride is from about 0.02 to about 1.0 percent by weight; and the cocophosphatidyl-dimonium chloride is from about 0.01 to about 1.0 percent by weight.

4. The composition of claim 1 wherein the naturally occurring plant or extract thereof is selected from the group consisting of curcuma longa, croccus sativus (saffron), alkanna tinctoria (henna root), hydrastis canadensis and mixtures thereof.

5. The composition of claim 4 wherein the amount of plant or plant extract is from about 0.1 to about 10 percent by weight based on individual plant or plant extract.

6. The composition of claim 1 which additionally contains an effective amount of diazolidinyl urea and 3-Iodo-propynylbutylcarbamate.

7. The composition of claim 6 wherein the total amount of diazolidinyl urea and 3-Iodo-propynylbutylcarbamate is from about 0.05 to about 0.5 percent by weight.

8. The composition of claim 6 which additionally contains an effective amount; methyl paraben, propyl paraben, and propylene glycol.

9. The composition of claim 8 wherein the total amount of diazolindinyl urea, methyl parabeni propyl paraben, and propylene glycol is from about 0.05 to about 0.5 percent by weight.

10. The composition of claim 1 which additionally contains an effective amount of cocamidopropyl phosphatidyl dimonium chloride.

11. The composition of claim 10 wherein the amount of cocamidopropyl phosphatidyl dimonium chloride is from about 0.01 to about 1.0 percent by weight.

12. A method of disinfecting a substrate comprising the step of applying to the substrate an effective amount of the antimicrobial composition of claim 1.

13. The method of claim 12 wherein the substrate is the hand.

14. A method for controlling intact and broken skin inflammations including local redness, local pain, local odour, increased exudate, and bacterial infections comprising topical administration to the skin an anti-inflammatory effective amount of the composition comprising:
    a) an antimicrobial selected from the group consisting of greater than 30% by volume alcohol, an effective amount of triclosan and mixtures thereof;
    b) an effective amount of phenoxy ethanol, benzalkonium chloride or benzethonium chloride, and cocophosphatidyl-dimonium chloride; and
    c) an effective amount of naturally occuring plant or plant extract.

15. A method for controlling skin inflammations and bacterial infections comprising topical administration to the skin an anti-inflammatory effective amount of the composition according to claim 4.

16. A method for controlling skin inflammations and bacterial infections selected from the group consisting of acne, skin lesions, pseudofolliculitis, local redness, local pain, local odor, and increased exudate comprising topical administration to the skin an anti-inflammatory effective amount of the composition comprising:
    a) an antimicrobial selected from the group consisting of greater than 30% by volume alcohol, an effective amount of triclosan and mixtures thereof;
    b) an effective amount of phenoxy ethanol, henzalkonium chloride or benzethonium chloride, and cocophosphatidyl-dimonium chloride, and
    c) an effective amount of naturally occurring plant or plant extract.

17. A method for controlling skin inflammations and bacterial infections selected from the group consisting of acne, skin lesions, pseudofolliculitis, local redness, local pain, local odor, and increased exudate comprising topical administration to the skin an anti-inflammatory effective amount of the composition of claim 4.

18. A gel comprising an effective amount of a, alcohol, an effective amount of phenoxy ethanol, benzalkonium chloride, cocophosphatidyl-dimonium chloride, and a naturally occurring plant or plant extract.

19. The gel of claim 18 wherein the naturally occurring plant or plant extract is selected from the group consisting of curcuma longa, croccus sativus (saffron), alkanna tinctoria (henna root), hydrastis canadensis and mixtures thereof.

20. The composition of claim 1 which additionally contains an effective amount of an essential oil selected from the group consisting of Australian tea tree oil, lemongrass oil, thyme oil lavender oil and clove oil.

21. The composition of claim 2 which additionally contains an effective amount of an essential oil selected from the group consisting of Australian tea tree oil, lemongrass oil, thyme oil lavender oil and clove oil.

22. The composition of claim 1 which additionally contains an effective amount of octanoyl collagenic acid and cetyl pyridinium chloride, and polyhexamethylene biguanide.

* * * * *